United States Patent [19]
Lovenberg et al.

[11] Patent Number: 6,136,559
[45] Date of Patent: Oct. 24, 2000

[54] DNA ENCODING AS HUMAN HISTAMINE RECEPTOR OF THE H3 SUBTYPE

[75] Inventors: Timothy W. Lovenberg, San Diego; Mark Erlander, Encinitas; Arne Huvar, Santee; Jayashree Pyati, San Diego, all of Calif.

[73] Assignee: Ortho Pharmaceutical Corporation, Raritan, N.J.

[21] Appl. No.: 09/167,354

[22] Filed: Oct. 7, 1998

[51] Int. Cl.[7] .......................... C12N 15/12; C12N 15/63; C12N 5/10; C07K 14/47; C07K 14/705
[52] U.S. Cl. ................ 435/69.1; 435/69.1; 435/70.3; 435/71.3; 435/71.2; 435/471; 435/325; 435/252.3; 435/320.1; 536/23.5; 536/24.3; 530/350
[58] Field of Search ................... 435/69.1, 70.3, 435/71.3, 71.2, 471, 325, 252.3, 320.1; 536/23.5, 24.3; 530/350

[56] References Cited

U.S. PATENT DOCUMENTS 5,817,480  10/1998  Murry et al. ..................... 435/69.1
5,882,893  3/1999   Goodearl ......................... 435/69.1

*Primary Examiner*—Gary L. Kunz
*Assistant Examiner*—Fozia Hamud
*Attorney, Agent, or Firm*—John W. Wallen, III

[57] ABSTRACT

DNAs encoding the human histamine H3 receptor have been cloned and characterized. The recombinant protein is capable of forming biologically active histamine H3 receptor protein. The cDNA's have been expressed in recombinant host cells which produce active recombinant protein. The recombinant protein is also purified from the recombinant host cells. In addition, the recombinant host cells are utilized to establish a method for identifying modulators of the receptor activity, and receptor modulators are identified.

4 Claims, 9 Drawing Sheets

FIG. 1A 2699 bases
CCACGCGTCCGCCGGCTGCACGGTCGCACCGGCAGCGGCTCAGGCTCCGG
CTCCTCTCCCGCTGCAGCAGCCGCGCTGCCGGCCCCACTGGGCTCGGATC
CGGCCCCGGCCCCCTCGGCACCGCCTGCTCTGGCCCCGGCCCCGGCCCCG
CGGACCATGCGCTGGGCGCCCCAGGGGAAACCCGACCCGGCCAAGGGCC
CGCAAAGACGAGGCTCCCGGGCCGGGCCCCTCCCGGCCGCCCAGCTCTC
GGCCGGCGCCCTGCCCCGCGTCCCGGAGCCGCGTGAGCCTGCGGGGCCAT
GGAGCGCGCCGCCCGACGGGCCGCTGAACGCTTCGGGGGCGCTGGCGG
GCGATGCGGCGGCGGCGGGCGGGGCGCGCGGCTTCTCGGCAGCCTGGACC
GCGGTGCTGGCCGCGCTCATGGCGCTGCTCATCGTGGCCACGGTGCTGGG
CAACGCGCTGGTCATGCTCGCCTTCGTGGCCGACTCGAGCCTCCGCACCC
AGAACAACTTCTTCCTGCTCAACCTCGCCATCTCCGACTTCCTCGTCGGC
GCCTTCTGCATCCCACTGTATGTACCCTACGTGCTGACAGGCCGCTGGAC
CTTCGGCCGGGGCCTCTGCAAGCTGTGGCTGGTAGTGGACTACCTGCTGT
GCACCTCCTCTGCCTTCAACATCGTGCTCATCAGCTACGACCGCTTCCTG
TCGGTCACCCGAGCGGTCTCATACCGGGCCCAGCAGGGTGACACGCGGCG
GGCAGTGCGGAAGATGCTGCTGGTGTGGGTGCTGGCCTTCCTGCTGTACG
GACCAGCCATCCTGAGCTGGGAGTACCTGTCCGGGGGCAGCTCCATCCCC
GAGGGCCACTGCTATGCCGAGTTCTTCTACAACTGGTACTTCCTCATCAC
GGCTTCCACCCTGGAGTTCTTTACGCCCTTCCTCAGCGTCACCTTCTTTA
ACCTCAGCATCTACCTGAACATCCAGAGGCGCACCCGCCTCCGGCTGGAT
GGGGCTCGAGAGGCAGCCGGCCCCGAGCCCCCTCCCGAGGCCCAGCCCTC
ACCACCCCCACCGCCTGGCTGCTGGGGCTGCTGGCAGAAGGGGCACGGGG
AGGCCATGCCGCTGCACAGGTATGGGGTGGGTGAGGCGGCCGTAGGCGCT
GAGGCCGGGGAGGCGACCCTCGGGGGTGGCGGTGGGGCGGCTCCGTGGC
TTCACCCACCTCCAGCTCCGGCAGCTCCTCGAGGGCACTGAGAGGCCGC
GCTCACTCAAGAGGGGCTCCAAGCCGTCGGCGTCCTCGGCCTCGCTGGAG
AAGCGCATGAAGATGGTGTCCCAGAGCTTCACCCAGCGCTTTCGGCTGTC
TCGGGACAGGAAAGTGGCCAAGTCGCTGGCCGTCATCGTGAGCATCTTTG
GGCTCTGCTGGGCCCCATACACGCTGCTGATGATCATCCGGGCCGCCTGC
CATGGCCACTGCGTCCCTGACTACTGGTACGAAACCTCCTTCTGGCTCCT
GTGGGCCAACTCGGCTGTCAACCCTGTCCTCTACCCTCTGTGCCACCACA
GCTTCCGCCGGGCCTTCACCAAGCTGCTCTGCCCCCAGAAGCTCAAAATC
CAGCCCCACAGCTCCCTGGAGCACTGCTGGAAGTGAGTGGCCCACCAGAG
CCTCCCTCAGCCACGCCTCTCTCAGCCCAGGTCTCCTGGGCATCTGGCCC
TGCTGCCCCCTACCCGGCTCGTTCCCCAGGGGTGAGCCCCGCCGTGTCT

FIG. 1B

GTGGCCCTCTCTTAATGCCACGGCAGCCACCCTGCCATGGAGGCGCCTTC
CTGGGTTGGCCAGAGGGCCCCTCACTGGCTGGACTGGAGGCTGGGTGGCC
GGCCCTGCCCCCCACATTCTGGCTCCACCGGGGAGGGACAGTCTGGAGGT
CCCAGACATGCTGCCCACCCCTGCTGGTGCCCACCCTTCGCAGTTACTG
GTTGGTGTTCTTCCCAAAGCAAGCACCTGGGTGTGCTCCAGGCTTCCTGC
CCTAGCAGTTTGCCTCTGCACGTGCACACACCTGCACACCCTGCACACA
CCTGCACACCGTCCCTCTCCCCGGACAAGCCCAGGACACTGCCTTTGCTG
CCTTCTGTCTCTTGCATAAGCCTCAGGCCTGGCCCTTTCACCCCTCTTCC
CACCAACTCTCTCTGCCCCCAAAAGTGTCAAGGGGCCCTAGGAACCTCGA
AGCTGTTCTCTGCTTTTCCATTCTGGGTGTTTTCAGAAAGATGAAGAAGA
AAACATGTCTGTGAACTTGATGTTCGTGGGATGTTTAATCAAGAGAGACA
AAATTGCTGAGGAGCTCAGGGCTGGATTGGCAGGTGTGGGCTCCCACGCC
CTCCTCCCTCCGCTAAGGCTTCCGGCTGAGCTGTGCCAGCTGCTTCTGCC
CACCCCGCCTCTGGGCTCACACCAGCCCTGGTGGCCAAGCCTGCCCCGGC
CACTCTGTTTGCTCACCCAGGACCTCTGGGGGTTGTTGGGAGGAGGGGGC
CCGGCTGGGCCCGAGGGTCCCAAGGCGTGCAGGGGCGGTCCAGAGGAGGT
GCCCGGGCAGGGGCCGCTTCGCCATGTGCTGTGCACCCGTGCCACGCGCT
CTGCATGCTCCTCTGCCTGTGCCCGCTGCGCTGCCCTGCAAACCGTGAGG
TCACAATAAAGTGTATTTTTTAAAAAAAAAAAAAAAAAAAAAAAAAAA
[SEQ.ID.NO.:5]

FIG. 2

1335
basesATGGAGCGCGCGCCGCCCGACGGGCCGCTGAACGCTTCGGGGGCGCTGGCGGGCGA
TGCGGCGGCGGCGGGCGGGGCGCGCGGCTTCTCGGCAGCCTGGACCGCGGTGCTGGCCGC
GCTCATGGCGCTGCTCATCGTGGCCACGGTGCTGGGCAACGCGCTGGTCATGCTCGCCTTC
GTGGCCGACTCGAGCCTCCGCACCCAGAACAACTTCTTCCTGCTCAACCTCGCCATCTCCG
ACTTCCTCGTCGGCGCCTTCTGCATCCCACTGTATGTACCCTACGTGCTGACAGGCCGCTG
GACCTTCGGCCGGGGCCTCTGCAAGCTGTGGCTGGTAGTGGACTACCTGCTGTGCACCTCC
TCTGCCTTCAACATCGTGCTCATCAGCTACGACCGCTTCCTGTCGGTCACCCGAGCGGTCT
CATACCGGGCCCAGCAGGGTGACACGCGGCGGGCAGTGCGGAAGATGCTGCTGGTGTGG
GTGCTGGCCTTCCTGCTGTACGGACCAGCCATCCTGAGCTGGGAGTACCTGTCCGGGGGC
AGCTCCATCCCCGAGGGCCACTGCTATGCCGAGTTCTTCTACAACTGGTACTTCCTCATCA
CGGCTTCCACCCTGGAGTTCTTTACGCCCTTCCTCAGCGTCACCTTCTTTAACCTCAGCATC
TACCTGAACATCCAGAGGCGCACCCGCCTCCGGCTGGATGGGGCTCGAGAGGCAGCCGGC
CCCGAGCCCCCTCCCGAGGCCCAGCCCTCACCACCCCCACCGCCTGGCTGCTGGGGCTGCT
GGCAGAAGGGGCACGGGGAGGCCATGCCGCTGCACAGGTATGGGGTGGGTGAGGCGGCC
GTAGGCGCTGAGGCCGGGGAGGCGACCCTCGGGGGTGGCGGTGGGGGCGGCTCCGTGGC
TTCACCCACCTCCAGCTCCGGCAGCTCCTCGAGGGGCACTGAGAGGCCGCGCTCACTCAA
GAGGGGCTCCAAGCCGTCGGCGTCCTCGGCCTCGCTGGAGAAGCGCATGAAGATGGTGTC
CCAGAGCTTCACCCAGCGCTTTCGGCTGTCTCGGGACAGGAAAGTGGCCAAGTCGCTGGC
CGTCATCGTGAGCATCTTTGGGCTCTGCTGGGCCCCATACACGCTGCTGATGATCATCCGG
GCCGCCTGCCATGGCCACTGCGTCCCTGACTACTGGTACGAAACCTCCTTCTGGCTCCTGT
GGGCCAACTCGGCTGTCAACCCTGTCCTCTACCCTCTGTGCCACCACAGCTTCCGCCGGGC
CTTCACCAAGCTGCTCTGCCCCAGAAGCTCAAAATCCAGCCCCACAGCTCCCTGGAGCA
CTGCTGGAAG[SEQ.ID.NO.:6]

FIG. 3

445 amino acids

Met Glu Arg Ala Pro Pro Asp Gly Pro Leu Asn Ala Ser Gly Ala Leu Ala Gly
Asp Ala Ala Ala Ala Gly Gly Ala Arg Gly Phe Ser Ala Ala Trp Thr Ala Val
Leu Ala Ala Leu Met Ala Leu Leu Ile Val Ala Thr Val Leu Gly Asn Ala Leu
Val Met Leu Ala Phe Val Ala Asp Ser Ser Leu Arg Thr Gln Asn Asn Phe Phe
Leu Leu Asn Leu Ala Ile Ser Asp Phe Leu Val Gly Ala Phe Cys Ile Pro Leu
Tyr Val Pro Tyr Val Leu Thr Gly Arg Trp Thr Phe Gly Arg Gly Leu Cys Lys
Leu Trp Leu Val Val Asp Tyr Leu Leu Cys Thr Ser Ser Ala Phe Asn Ile Val
Leu Ile Ser Tyr Asp Arg Phe Leu Ser Val Thr Arg Ala Val Ser Tyr Arg Ala
Gln Gln Gly Asp Thr Arg Arg Ala Val Arg Lys Met Leu Leu Val Trp Val Leu
Ala Phe Leu Leu Tyr Gly Pro Ala Ile Leu Ser Trp Glu Tyr Leu Ser Gly Gly
Ser Ser Ile Pro Glu Gly His Cys Tyr Ala Glu Phe Phe Tyr Asn Trp Tyr Phe
Leu Ile Thr Ala Ser Thr Leu Glu Phe Phe Thr Pro Phe Leu Ser Val Thr Phe
Phe Asn Leu Ser Ile Tyr Leu Asn Ile Gln Arg Arg Thr Arg Leu Arg Leu Asp
Gly Ala Arg Glu Ala Ala Gly Pro Glu Pro Pro Glu Ala Gln Pro Ser Pro
Pro Pro Pro Pro Gly Cys Trp Gly Cys Trp Gln Lys Gly His Gly Glu Ala Met
Pro Leu His Arg Tyr Gly Val Gly Glu Ala Ala Val Gly Ala Glu Ala Gly Glu
Ala Thr Leu Gly Gly Gly Gly Gly Gly Ser Val Ala Ser Pro Thr Ser Ser
Ser Gly Ser Ser Ser Arg Gly Thr Glu Arg Pro Arg Ser Leu Lys Arg Gly Ser
Lys Pro Ser Ala Ser Ser Ala Ser Leu Glu Lys Arg Met Lys Met Val Ser Gln
Ser Phe Thr Gln Arg Phe Arg Leu Ser Arg Asp Arg Lys Val Ala Lys Ser Leu
Ala Val Ile Val Ser Ile Phe Gly Leu Cys Trp Ala Pro Tyr Thr Leu Leu Met
Ile Ile Arg Ala Ala Cys His Gly His Cys Val Pro Asp Tyr Trp Tyr Glu Thr
Ser Phe Trp Leu Leu Trp Ala Asn Ser Ala Val Asn Pro Val Leu Tyr Pro Leu
Cys His His Ser Phe Arg Arg Ala Phe Thr Lys Leu Leu Cys Pro Gln Lys Leu
Lys Ile Gln Pro His Ser Ser Leu Glu His Cys Trp Lys

[SEQ.ID.NO.:7]

FIG. 4

PCR-based distribution of human histamine H3 receptor

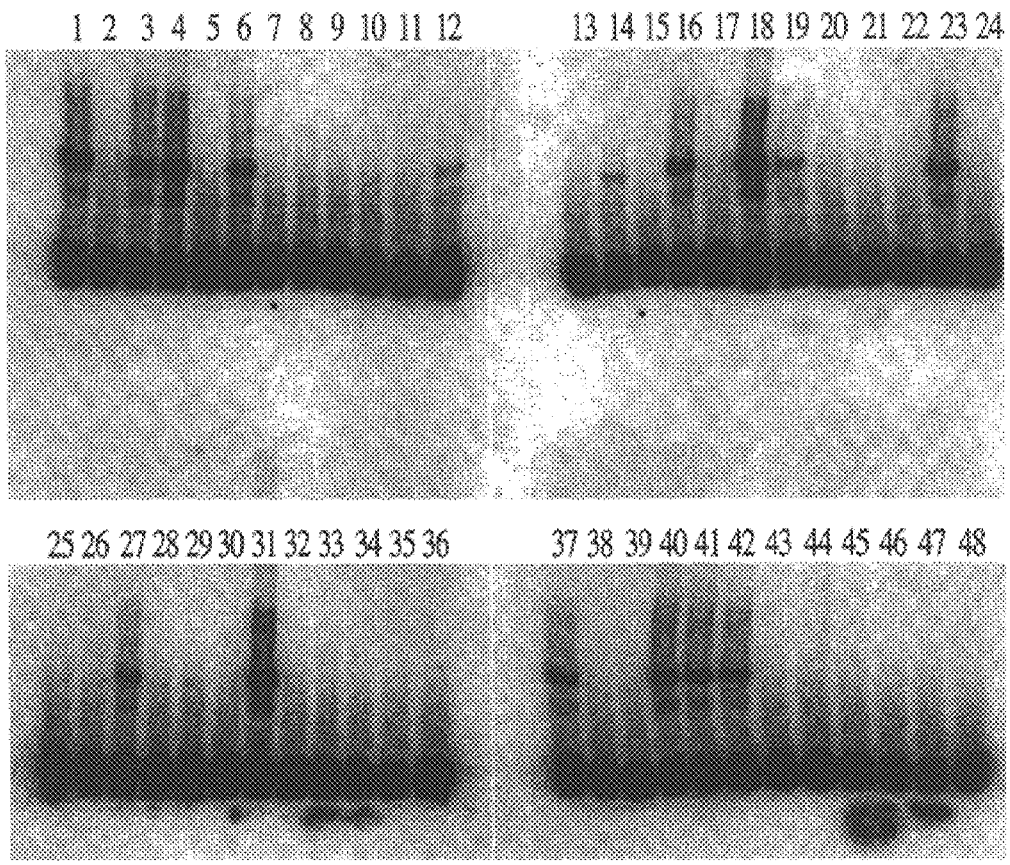

1, Amygdala; 2, Bone Marrow; 3, Brain; 4, Cerebellum; 5, Heart; 6, Hippocampus; 7, Kidney; 8, Liver; 9, Lung; 10, Pancreas; 11, Placenta; 12, Prostate; 13, Skeletal Muscle; 14, Small Intestine; 15, Spleen; 16, Spinal Cord; 17, Stomach; 18, Thalamus; 19, Testis; 20, Thymus; 21, Uterus; 22, Adrenal Gland; 23, Caudate Nucleus; 24, Lymph Node; 25, Mammary Gland; 26, Salivary Gland; 27, Substantia Nigra; 28, Thyroid; 29, Trachea; 30 Spleen; 31, Thalamus; 32, Placenta; 33, Heart; 34, Liver; 35, Lung; 36, Uterus; 37, Pituitary; 38, Spinal cord; 39, Bone Marrow; 40, Hippocampus; 41, Dorsal Root Ganglia; 42, Small Intestine; 43, Negative Control; 44, Negative Control; 45, Negative Control; 46, Negative Control; 47, Negative Control; 48, Negative Control.

a-methyl-HA = H3 agonist alpha-methyl-histamine (1uM)
HA = Histamine (1uM)
H1 antagonist = diphenhydramine (10uM)
H2 antagonist = ranitidine (10uM)
H3 antagonist = thioperamide (10uM)

FIG. 6

ACTGGTACGAAACCTCCTTCTGGCTCCTGTGGG<u>CCAACTCGGCTGTCAACC
CTGTCCT</u>CTACCCTCTGTGCCACCACAGCTTCCGCCGGGCCTTCACCAAGC
TGCTCTGCCCCAGAAGCTCAAAATCCAGCCCCACAGCTCCCTGGAGCAC
TGCTGGAAGTGAGTGGCCCACCAGAGCCTCCCTCAGCCACGCCTCTCTCA
GCCCAGGTCTCCTGGGCATCTGGCCCTGCTGCCCCTACCCGGCTCGTTCC
CCCAGGGGTGAGCCCCGCCGTGTCTGTGGCCCTCTCTTAATGCCACGGCA
GCCACCCTGCCATGGAGGCGCCTTCCTGGGTTGGCCAGAGGGCCCCTCAC
TGGCTGGACTGGAGGCTGGGTG [SEQ.ID.NO.:8]

SEQUENCE LISTING

<160> NUMBER OF SEQ ID NOS: 8

<210> SEQ ID NO 1
<211> LENGTH: 26

```
<212> TYPE: DNA
<213> ORGANISM: Artificial Sequence
<220> FEATURE:
<223> OTHER INFORMATION: Description of Artificial Sequence: CDNA

<400> SEQUENCE: 1
actggtacga aacctccttc tggctc                                             26

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: CDNA

<400> SEQUENCE: 2
cacccagcct ccagtccagc cagtgag                                            27

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: CDNA

<400> SEQUENCE: 3
aacgttgaat tcgccaccat ggagcgcgcg ccgcccgacg ggccgctgaa c                 51

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: CDNA

<400> SEQUENCE: 4
aacgttgcgg ccgcaggctc tggtgggcca ctcacttcca g                            41

<210> SEQ ID NO 5
<211> LENGTH: 2699
<212> TYPE: DNA
<213> ORGANISM: Artificial Sequence
<220> FEATURE:
<223> OTHER INFORMATION: Description of Artificial Sequence: CDNA

<400> SEQUENCE: 5
ccacgcgtcc gccggctgca cggtcgcacc ggcagcggct caggctccgg ctcctctccc         60
gctgcagcag ccgcgctgcc ggccccactg ggctcggatc cggccccggc cccctcggca        120
ccgcctgctc tggccccggc cccggccccg cggaccatgc gctgggcgcc cccagggaa         180 acccgacccg gccaagggcc cgcaaagacg aggctcccgg gccggggccc ctcccggccg        240
cccagctctc ggccggcgcc ctgccccgcg tcccggagcc gcgtgagcct gcggggccat        300
ggagcgcgcg ccgcccgacg ggccgctgaa cgcttcgggg gcgctggcgg gcgatgcggc        360
ggcggcgggc ggggcgcgcg gcttctcggc agcctgacc gcggtgctgg ccgcgctcat        420
ggcgctgctc atcgtggcca cggtgctggg caacgcgctg gtcatgctcg ccttcgtggc        480
cgactcgagc ctccgcaccc agaacaactt cttcctgctc aacctcgcca tctccgactt        540
cctcgtcggc gccttctgca tcccactgta tgtacctac gtgctgacag gccgctggac        600
cttcggccgg ggcctctgca agctgtggct ggtagtggac taccattcgt gcacctcctc        660
tgccttcaac atcgtgctca tcagctacga ccgcttcctg tcggtcaccc gagcggtctc        720
```

-continued

```
ataccgggcc cagcagggtg acacgcggcg ggcagtgcgg aagatgctgc tggtgtgggt        780
gctggccttc ctgctgtacg gaccagccat cctgagctgg gagtacctgt ccggggggcag       840 ctccatcccc gagggccact gctatgccga gttcttctac aactggtact tcctcatcac        900
ggcttccacc ctggagttct ttacgccctt cctcagcgtc accttcttta acctcagcat        960
ctacctgaac atccagaggc gcacccgcct ccggctggat ggggctcgag aggcagccgg        1020
ccccgagccc cctcccgagg cccagccctc accaccccca ccgcctggct gctggggctg        1080
ctggcagaag gggcacgggg aggccatgcc gctgcacagg tatggggtgg gtgaggcggc        1140
cgtaggcgct gaggccgggg aggcgaccct cgggggtggc ggtggggcg gctccgtggc         1200 ttcacccacc tccagctccg gcagctcctc gagggcact gagaggccgc gctcactcaa         1260 gagggctcc aagccgtcgg cgtcctcggc ctcgctggag aagcgcatga agatggtgtc        1320
ccagagcttc acccagcgct ttcggctgtc tcgggacagg aaagtggcca agtcgctggc       1380
cgtcatcgtg agcatctttg ggctctgctg ggccccatac acgctgctga tgatcatccg       1440
ggccgcctgc catggccact gcgtccctga ctactggtac gaaacctcct tctggctcct       1500
gtgggccaac tcggctgtca accctgtcct ctaccctctg tgccaccaca gcttccgccg       1560
ggccttcacc aagctgctct gccccagaa gctcaaaatc cagccccaca gctccctgga       1620
gcactgctgg aagtgagtgg cccaccagag cctccctcag ccacgcctct ctcagcccag       1680
gtctcctggg catctggccc tgctgccccc tacccggctc gttccccag gggtgagccc        1740 cgccgtgtct gtgccctct cttaatgcca cggcagccac cctgccatgg aggcgccttc        1800
ctgggttggc cagagggccc ctcactggct ggactggagg ctgggtggcc ggccctgccc       1860
cccacattct ggctccaccg gggagggaca gtctggaggt cccagacatg ctgcccaccc      1920
cctgctggtg cccacccttc gcagttactg gttggtgttc ttcccaaagc aagcacctgg      1980
gtgtgctcca ggcttcctgc cctagcagtt tgcctctgca cgtgcacaca cctgcacacc      2040
cctgcacaca cctgcacacc gtccctctcc ccggacaagc caggacact gcctttgctg      2100 ccttctgtct cttgcataag cctcaggcct ggccctttca cccctcttcc caccaactct      2160
ctctgccccc aaaagtgtca agggggccta ggaacctcga agctgttctc tgcttttcca       2220
ttctgggtgt tttcagaaag atgaagaaga aaacatgtct gtgaacttga tgttcgtggg       2280
atgtttaatc aagagagaca aaattgctga ggagctcagg gctggattgg caggtgtggg       2340
ctcccacgcc ctcctccctc cgctaaggct tccggctgag ctgtgccagc tgcttctgcc       2400 cacccgcct ctgggctcac accagccctg gtggccaagc ctgccccggc cactctgttt       2460
gctcacccag gacctctggg ggttgttggg aggaggggc ccggctgggc ccgagggtcc       2520
caaggcgtgc aggggcggtc cagaggaggt gcccgggcag gggccgcttc gccatgtgct      2580
gtgcacccgt gccacgcgct ctgcatgctc ctctgcctgt gcccgctgcg ctgccctgca      2640
aaccgtgagg tcacaataaa gtgtattttt ttaaaaaaaa aaaaaaaaaa aaaaaaaa        2699
```

<210> SEQ ID NO 6
<211> LENGTH: 1335
<212> TYPE: DNA
<213> ORGANISM: Artificial Sequence
<220> FEATURE:
<223> OTHER INFORMATION: Description of Artificial Sequence:CDNA

<400> SEQUENCE: 6

```
atggagcgcg cgccgcccga cgggccgctg aacgcttcgg gggcgctggc gggcgatgcg        60
gcggcggcgg gcggggcgcg cggcttctcg gcagcctgga ccgcggtgct ggccgcgctc       120
```

```
atgcgctgc tcatcgtggc cacggtgctg ggcaacgcgc tggtcatgct cgccttcgtg      180
gccgactcga gcctccgcac ccagaacaac ttcttcctgc tcaacctcgc catctccgac      240
ttcctcgtcg gcgccttctg catcccactg tatgtaccct acgtgctgac aggccgctgg      300
accttcggcc ggggcctctg caagctgtgg ctggtagtgg actacctgct gtgcacctcc      360
tctgccttca acatcgtgct catcagctac gaccgcttcc tgtcggtcac ccgagcggtc      420
tcataccggg cccagcaggg tgacacgcgc cgggcagtgc ggaagatgct gctggtgtgg      480
gtgctggcct tcctgctgta cggaccagcc atcctgagct gggagtacct gtccgggggc      540
agctccatcc ccgagggcca ctgctatgcc gagttcttct acaactggta cttcctcatc      600
acggcttcca ccctggagtt ctttacgccc ttcctcagcg tcaccttctt taacctcagc      660
atctacctga acatccagag gcgcacccgc ctccggctgg atgggctcga gaggcagcc       720 ggccccgagc ccctcccga ggcccagccc tcaccacccc caccgcctgg ctgctggggc        780
tgctggcaga aggggcacgg ggaggccatg ccgctgcaca ggtatggggt gggtgaggcg      840
gccgtaggcg ctgaggccgg ggaggcgacc ctcggggtg gcggtgggg cggctccgtg        900 gcttcaccca cctccagctc cggcagctcc tcgaggggca ctgagaggcc gcgctcactc      960 aagagggct ccaagccgtc ggcgtcctcg gcctcgctgg agaagcgcat gaagatggtg        1020
tcccagagct tcacccagcg ctttcggctg tctcgggaca ggaaagtggc caagtcgctg      1080
gccgtcatcg tgagcatctt tgggctctgc tgggccccat acacgctgct gatgatcatc      1140
cgggccgcct gccatggcca ctgcgtccct gactactggt acgaaacctc cttctggctc      1200
ctgtgggcca actcggctgt caaccctgtc ctctaccctc tgtgccacca cagcttccgc      1260
cgggccttca ccaagctgct ctgcccccag aagctcaaaa tccagcccca cagctccctg      1320
gagcactgct ggaag                                                        1335
```

<210> SEQ ID NO 7
<211> LENGTH: 445
<212> TYPE: PRT
<213> ORGANISM: Artificial Sequence
<220> FEATURE:
<223> OTHER INFORMATION: Description of Artificial Sequence:PEPTIDE

<400> SEQUENCE: 7

```
Met Glu Arg Ala Pro Pro Asp Gly Pro Leu Asn Ala Ser Gly Ala Leu
  1               5                  10                  15

Ala Gly Asp Ala Ala Ala Gly Gly Ala Arg Gly Phe Ser Ala Ala
             20                  25                  30

Trp Thr Ala Val Leu Ala Ala Leu Met Ala Leu Leu Ile Val Ala Thr
         35                  40                  45

Val Leu Gly Asn Ala Leu Val Met Leu Ala Phe Val Ala Asp Ser Ser
     50                  55                  60

Leu Arg Thr Gln Asn Asn Phe Phe Leu Leu Asn Leu Ala Ile Ser Asp
 65                  70                  75                  80

Phe Leu Val Gly Ala Phe Cys Ile Pro Leu Tyr Val Pro Tyr Val Leu
                 85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
        115                 120                 125

Ser Tyr Asp Arg Phe Leu Ser Val Thr Arg Ala Val Ser Tyr Arg Ala
    130                 135                 140
```

Gln Gln Gly Asp Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
            165                 170                 175

Leu Ser Gly Gly Ser Ser Ile Pro Glu Gly His Cys Tyr Ala Glu Phe
            180                 185                 190

Phe Tyr Asn Trp Tyr Phe Leu Ile Thr Ala Ser Thr Leu Glu Phe Phe
            195                 200                 205

Thr Pro Phe Leu Ser Val Thr Phe Phe Asn Leu Ser Ile Tyr Leu Asn
210                 215                 220

Ile Gln Arg Arg Thr Arg Leu Arg Leu Asp Gly Ala Arg Glu Ala Ala
225                 230                 235                 240

Gly Pro Glu Pro Pro Glu Ala Gln Pro Ser Pro Pro Pro Pro
            245                 250                 255

Gly Cys Trp Gly Cys Trp Gln Lys Gly His Gly Glu Ala Met Pro Leu
            260                 265                 270

His Arg Tyr Gly Val Gly Glu Ala Val Gly Ala Glu Ala Gly Glu
            275                 280                 285

Ala Thr Leu Gly Gly Gly Gly Gly Ser Val Ala Ser Pro Thr
290                 295                 300

Ser Ser Ser Gly Ser Ser Ser Arg Gly Thr Glu Arg Pro Arg Ser Leu
305                 310                 315                 320

Lys Arg Gly Ser Lys Pro Ser Ala Ser Ser Ala Ser Leu Glu Lys Arg
            325                 330                 335

Met Lys Met Val Ser Gln Ser Phe Thr Gln Arg Phe Arg Leu Ser Arg
            340                 345                 350

Asp Arg Lys Val Ala Lys Ser Leu Ala Val Ile Val Ser Ile Phe Gly
            355                 360                 365

Leu Cys Trp Ala Pro Tyr Thr Leu Leu Met Ile Ile Arg Ala Ala Cys
370                 375                 380

His Gly His Cys Val Pro Asp Tyr Trp Tyr Glu Thr Ser Phe Trp Leu
385                 390                 395                 400

Leu Trp Ala Asn Ser Ala Val Asn Pro Val Leu Tyr Pro Leu Cys His
            405                 410                 415

His Ser Phe Arg Arg Ala Phe Thr Lys Leu Leu Cys Pro Gln Lys Leu
            420                 425                 430

Lys Ile Gln Pro His Ser Ser Leu Glu His Cys Trp Lys
            435                 440                 445

<210> SEQ ID NO 8
<211> LENGTH: 375
<212> TYPE: DNA
<213> ORGANISM: Artificial Sequence
<220> FEATURE:
<223> OTHER INFORMATION: Description of Artificial Sequence:CDNA

<400> SEQUENCE: 8
actggtacga aacctccttc tggctcctgt gggccaactc ggctgtcaac cctgtcctct    60
accctctgtg ccaccacagc ttccgccggg ccttcaccaa gctgctctgc ccccagaagc   120
tcaaaatcca gccccacagc tccctggagc actgctggaa gtgagtggcc caccagagcc   180
tccctcagcc acgcctctct cagcccaggt ctcctgggca tctggccctg ctgccccta   240

-continued

```
cccggctcgt tcccccaggg gtgagcccccg ccgtgtctgt ggccctctct taatgccacg      300
gcagccaccc tgccatggag gcgccttcct gggttggcca gagggcccct cactggctgg      360
actggaggct gggtg                                                       375
```

DNA ENCODING AS HUMAN HISTAMINE RECEPTOR OF THE H3 SUBTYPE

BACKGROUND OF THE INVENTION

Histamine is a multifunctional chemical transmitter that signals through cell surface receptors that are linked to intracellular pathways via guanine nucleotide binding proteins. This class of cell surface receptors are called G-protein coupled receptors or GPCRs. There are currently three subtypes of histamine receptors that have been defined pharmacologically and have been divided into H1, H2, and H3 classifications (Hill, et al. 1997). The H1 histamine receptor has been cloned (Yamashita, et al. 1991)and is the target of drugs such as diphenhydramine to block the effects of histamine in allergic responses. The H2 histamine receptor has been cloned (Gantz et al. 1991) and is the target of drugs such as ranitidine to block the effects of histamine on acid secretion in the stomach. The third subtype of histamine receptor was hypothesized to exist in 1983 (Arrang, et al. 1983). It is believed to function as a presynaptic autoreceptor in histamine containing neurons in the central nervous system and as a presynaptic heteroreceptor in non-histamine containing neurons. One of the functions of the H3 receptor is to regulate neurotransmitter release at the presynaptic site. Histamine H3 receptors are thus expressed in the central nervous system, but have also been pharmacologically identified in heart, lung, and stomach, and have been hypothesized to exist in other tissues.

The present invention relates to the isolation and characterization of a human cDNA encoding a histamine H3 receptor and the uses thereof. z

SUMMARY OF THE INVENTION

A DNA molecule encoding a human histamine H3 receptor has been cloned and characterized and it represents a novel member of the class of receptors that couple to G-proteins. Using a recombinant expression system functional DNA molecules encoding the human histamine H3 receptor have been isolated. The biological and structural properties of these proteins are disclosed, as is the amino acid and nucleotide sequence. The recombinant protein is useful for a variety of purposes, including but not limited to identifying modulators of the human histamine H3 receptor. Modulators identified in the assays disclosed herein are useful, for example, as therapeutic agents, and diagnostic agents. Indications for said therapeutic agents include, but are not limited to, central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behavior, panic attacks, pain, social phobias, eating disorders and anorexia, cardiovascular and cerebrovascular disorders, non-insulin dependent diabetes mellitus, hyperglycemia, constipation, arrhythmia, disorders of the neuroendrocrine system, stress, and spasticity, as well as acid secretin, ulcers, airway constriction, asthma, allergy, inflammation, and prostate dysfunction. The recombinant DNA molecules, and portions thereof, are useful for isolating homologues of the DNA molecules, identifying and isolating genomic equivalents of the DNA molecules, and identifying, detecting or isolating mutant forms of the DNA molecules.

BRIEF DESCRIPTION OF THE DRAWING

FIG. 1—The complete nucleotide sequence of human histamine H3 receptor including untranslated regions is shown.

FIG. 2—The nucleotide sequence of the coding region for the human histamine H3 receptor is shown.

FIG. 3—The amino acid sequence of human histamine H3 receptor is shown.

FIG. 4—The tissue distribution of the human histamine H3 receptor is shown.

FIG. 6—The nucleotide sequence of the pH3R probe is shown.

DETAILED DESCRIPTION

Figure 5:
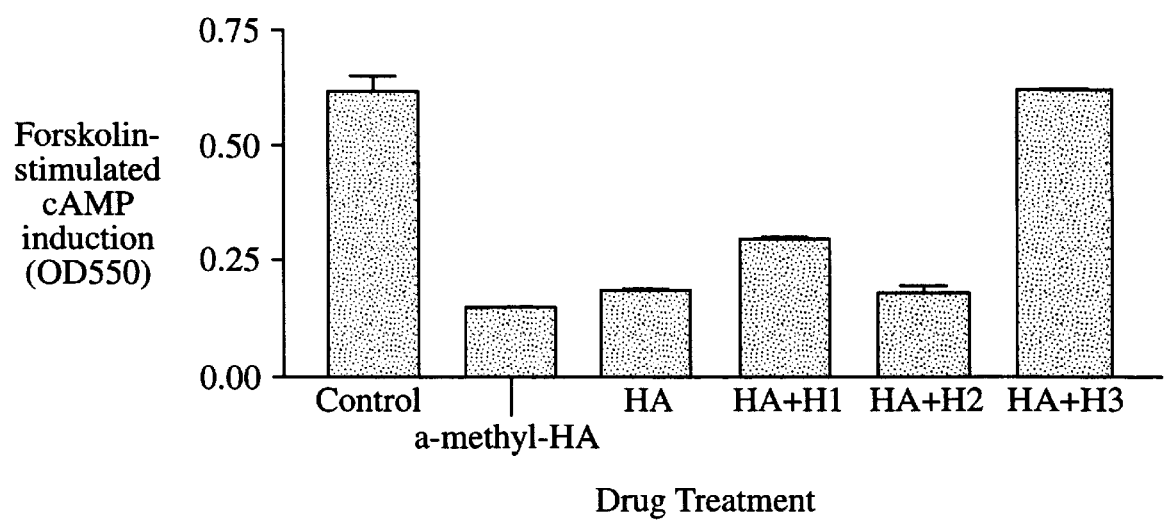
FIG. 5—Modulation of human histamine H3 receptor by a known H3 agonists (R-alpha-methylhistamine) and a known H3 antagonist (thioperamide) is shown.

The present invention relates to DNA encoding human histamine H3 receptor which was isolated from a cDNA library from human thalamus. The human histamine H3 receptor, as used herein, refers to protein which can specifically function as a receptor for histamine of the H3 subclass.

The complete amino acid sequence of human histamine H3 receptor was not previously known, nor was the complete nucleotide sequence encoding human histamine H3 receptor known. This is the first reported cloning of a full length DNA molecule encoding human histamine H3 receptor. It is predicted that a wide variety of cells and cell types will contain the described human histamine H3 receptor. Vertebrate cells capable of producing human histamine H3 receptor include, but are not limited to human histamine H3 receptor cells isolated from cells that show sensitivity to or bind histamine. Other cells and cell lines may also be suitable for use to isolate human histamine H3 receptor cDNA. Selection of suitable cells may be done by screening for inhibition of adenylate cyclase in response to histamine. Human histamine H3 receptor activity can be monitored by performing a $^3$H-alphamethylhistamine binding assay (Pollard, Moreau et al. 1993)or by direct measurment of inhibition of adenylate cyclase due to human histamine H3 receptor activation or by incorporation of GTP-gamma-S (Clark, Korte et al. 1993) Cells which possess human histamine H3 receptor activity in this assay may be suitable for the isolation of human histamine H3 receptor DNA or mRNA.

Any of a variety of procedures known in the art may be used to molecularly clone human histamine H3 receptor DNA. These methods include, but are not limited to, direct functional expression of the human histamine H3 receptor genes following the construction of a human histamine H3 receptor-containing cDNA library in an appropriate expression vector system. Another method is to screen human histamine H3 receptor-containing cDNA library constructed in a bacteriophage or plasmid shuttle vector with a labelled oligonucleotide probe designed from the amino acid sequence of the human histamine H3 receptor subunits. An additional method consists of screening a human histamine H3 receptor-containing cDNA library constructed in a bacteriophage or plasmid shuttle vector with a partial cDNA encoding the human histamine H3 receptor protein. This partial cDNA is obtained by the specific PCR amplification of human histamine H3 receptor DNA fragments through the design of degenerate oligonucleotide primers from the amino acid sequence of the purified human histamine H3 receptor protein.

Another method is to isolate RNA from human histamine H3 receptor-producing cells and translate the RNA into protein via an in vitro or an in vivo translation system. The translation of the RNA into a peptide or a protein will result in the production of at least a portion of the human histamine H3 receptor protein which can be identified by, for example, immunological reactivity with an anti-human histamine H3 receptor antibody or by biological activity of human histamine H3 receptor protein. In this method, pools of RNA isolated from human histamine H3 receptor-producing cells can be analyzed for the presence of an RNA which encodes at least a portion of the human histamine H3 receptor protein. Further fractionation of the RNA pool can be done to purify the human histamine H3 receptor RNA from non-human histamine H3 receptor RNA. The peptide or protein produced by this method may be analyzed to provide amino acid sequences which in turn are used to provide primers for production of human histamine H3 receptor cDNA, or the RNA used for translation can be analyzed to provide nucleotide sequences encoding human histamine H3 receptor and produce probes for this production of human histamine H3 receptor cDNA. This method is known in the art and can be found in, for example, Maniatis, T., Fritsch, E. F., Sambrook, J. in Molecular Cloning: A Laboratory Manual, Second Edition, Cold Spring Harbor Laboratory Press, Cold Spring Harbor, N.Y. 1989.

It is readily apparent to those skilled in the art that other types of libraries, as well as libraries constructed from other cells or cell types, may be useful for isolating human histamine H3 receptor-encoding DNA. Other types of libraries include, but are not limited to, cDNA libraries derived from other cells, from organisms other than human, and genomic DNA libraries that include YAC (yeast artificial chromosome) and cosmid libraries.

It is readily apparent to those skilled in the art that suitable cDNA libraries may be prepared from cells or cell lines which have human histamine H3 receptor activity. The selection of cells or cell lines for use in preparing a cDNA library to isolate human histamine H3 receptor cDNA may be done by first measuring cell associated human histamine H3 receptor activity using the measurment of human histamine H3 receptor-associated biological activity or a $^3$H-histamine ligand binding assay or $^3$H-N-methylhistamine ligand binding assay or any radioligand binding involving a ligand that has the ability to bind to the human histamine H3 receptor.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual, Second Edition (Cold Spring Harbor Laboratory, Cold Spring Harbor, N.Y., 1989).

It is also readily apparent to those skilled in the art that DNA encoding human histamine H3 receptor may also be isolated from a suitable genomic DNA library. Construction of genomic DNA libraries can be performed by standard techniques well known in the art. Well known genomic DNA library construction techiques can be found in Maniatis, T., Fritsch, E. F., Sambrook, J. in Molecular Cloning: A Laboratory Manual, Second Edition (Cold Spring Harbor Laboratory, Cold Spring Harbor, N.Y., 1989).

In order to clone the human histamine H3 receptor gene by the above methods, the amino acid sequence of human histamine H3 receptor may be necessary. To accomplish this, human histamine H3 receptor protein may be purified and partial amino acid sequence determined by automated sequenators.

It is not necessary to determine the entire amino acid sequence, but the linear sequence of two regions of 6 to 8 amino acids from the protein is determined for the production of primers for PCR amplification of a partial human histamine H3 receptor DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the human histamine H3 receptor sequence but will be capable of hybridizing to human histamine H3 receptor DNA even in the presence of DNA oligonucleotides with mismatches. The mismatched DNA oligonucleotides may still sufficiently hybridize to the human histamine H3 receptor DNA to permit identification and isolation of human histamine H3 receptor encoding DNA. DNA isolated by these methods can be used to screen DNA libraries from a variety of cell types, from invertebrate and vertebrate sources, and to isolate homologous genes.

Purified biologically active human histamine H3 receptor may have several different physical forms. Human histamine H3 receptor may exist as a full-length nascent or unprocessed polypeptide, or as partially processed polypeptides or combinations of processed polypeptides. The full-length nascent human histamine H3 receptor polypeptide may be post-translationally modified by specific proteolytic cleavage events which result in the formation of fragments of the full length nascent polypeptide. A fragment, or physical association of fragments may have the full biological activity associated with human histamine H3 receptor however, the degree of human histamine H3 receptor activity may vary between individual human histamine H3 receptor fragments and physically associated human histamine H3 receptor polypeptide fragments.

The cloned human histamine H3 receptor DNA obtained through the methods described herein may be recombinantly expressed by molecular cloning into an expression vector containing a suitable promoter and other appropriate transcription regulatory elements, and transferred into prokaryotic or eukaryotic host cells to produce recombinant human histamine H3 receptor protein. Techniques for such manipulations are fully described in Maniatis, T. et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including E. coli, bluegreen algae, plant cells, insect cells, fungal cells including yeast cells, and animal cells. Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant human histamine H3 receptor in mammalian cells. Commercially available mammalian expression vectors which may be suitable for recombinant human histamine H3 receptor expression, include but are not limited to, pMAMneo (Clontech), pcDNA3 (Invitrogen), pMC1neo (Stratagene), pXT1 (Stratagene), pSG5 (Stratagene), pCIneo (Promega), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

A variety of bacterial expression vectors may be used to express recombinant human histamine H3 receptor in bacterial cells. Commercially available bacterial expression vectors which may be suitable for recombinant human histamine H3 receptor expression include, but are not limited to pET vectors (Novagen) and pQE vectors (Qiagen).

A variety of fungal cell expression vectors may be used to express recombinant human histamine H3 receptor in fungal cells such as yeast.

Commerically available fungal cell expression vectors which may be suitable for recombinant human histamine H3 receptor expression include but are not limited to pYES2 (Invitrogen) and Pichia expression vector (Invitrogen).

A variety of insect cell expression vectors may be used to express recombinant human histamine H3 receptor in insect cells. Commercially available insect cell expression vectors which may be suitable for recombinant expression of human histamine H3 receptor include but are not limited to pBlue-BacII (Invitrogen).

DNA encoding human histamine H3 receptor may be cloned into an expression vector for expression in a recombinant host cell. Recombinant host cells may be prokaryotic or eukaryotic, including but not limited to bacteria such as *E. coli*, fungal cells such as yeast, mammalian cells including but not limited to cell lines of human, bovine, porcine, monkey and rodent origin, and insect cells including but not limited to drosophila and silkworm derived cells. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce human histamine H3 receptor protein. Identification of human histamine H3 receptor expressing host cell clones may be done by several means, including but not limited to immunological reactivity with anti-human histamine H3 receptor antibodies, and the presence of host cell-associated human histamine H3 receptor activity.

Expression of human histamine H3 receptor DNA may also be performed using in vitro produced synthetic mRNA. Synthetic mRNA or mRNA isolated from human histamine H3 receptor producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being generally preferred.

To determine the human histamine H3 receptor DNA sequence(s) that yields optimal levels of human histamine H3 receptor activity and/or human histamine H3 receptor protein, human histamine H3 receptor DNA molecules including, but not limited to, the following can be constructed: the full-length open reading frame of the human histamine H3 receptor cDNA encoding the 48656 kDa protein from approximately base 299 to approximately base 1634 (these numbers correspond to first nucleotide of first methionine and last nucleotide before the first stop codon) and several constructs containing portions of the cDNA encoding human histamine H3 receptor protein. All constructs can be designed to contain none, all or portions of the 5' or the 3' untranslated region of human histamine H3 receptor cDNA. Human histamine H3 receptor activity and levels of protein expression can be determined following the introduction, both singly and in combination, of these constructs into appropriate host cells. Following determination of the human histamine H3 receptor DNA cassette yielding optimal expression in transient assays, this human histamine H3 receptor DNA construct is transferred to a variety of expression vectors, for expression in host cells including, but not limited to, mammalian cells, baculovirus-infected insect cells, *E. coli*, and the yeast *S. cerevisiae*.

Host cell transfectants and microinjected oocytes may be used to assay both the levels of human histamine H3 receptor activity and levels of human histamine H3 receptor protein by the following methods. In the case of recombinant host cells, this involves the co-transfection of one or possibly two or more plasmids, containing the human histamine H3 receptor DNA encoding one or more fragments or subunits. In the case of oocytes, this involves the co-injection of RNAs encoding human histamine H3 receptor protein. Following an appropriate period of time to allow for expression, cellular protein is metabolically labelled with, for example $^{35}$S-methionine for 24 hours, after which cell lysates and cell culture supernatants are harvested and subjected to immunprecipitation with polyclonal antibodies directed against the human histamine H3 receptor protein.

Other methods for detecting human histamine H3 receptor activity involve the direct measurement of human histamine H3 receptor activity in whole cells transfected with human histamine H3 receptor cDNA or oocytes injected with human histamine H3 receptor mRNA. Human histamine H3 receptor activity is measured by specific ligand binding and biological characteristics of the host cells expressing human histamine H3 receptor DNA. In the case of recombinant host cells and oocytes expressing human histamine H3 receptor cAMP quantitation and receptor binding techniques are suitable examples of methods that can be used to measure human histamine H3 receptor activity and quantitate human histamine H3 receptor protein.

Levels of human histamine H3 receptor protein in host cells are also quantitated by immunoaffinity and/or ligand affinity techniques. Cells expressing human histamine H3 receptor can be assayed for the number of human histamine H3 receptor molecules expressed by measuring the amount of radioactive histamine or histamine H3 ligand binding to cell membranes. Human histamine H3 receptor-specific affinity beads or human histamine H3 receptor-specific antibodies are used to isolate for example $^{35}$S-methionine labelled or unlabelled human histamine H3 receptor protein. Labelled human histamine H3 receptor protein is analyzed by SDS-PAGE. Unlabelled human histamine H3 receptor protein is detected by Western blotting, ELISA or RIA assays employing human histamine H3 receptor specific antibodies.

Because the genetic code is degenerate, more than one codon may be used to encode a particular amino acid, and therefore, the amino acid sequence can be encoded by any of a set of similar DNA oligonucleotides. Only one member of the set will be identical to the human histamine H3 receptor sequence but will be capable of hybridizing to human histamine H3 receptor DNA even in the presence of DNA oligonucleotides with mismatches under appropriate conditions. Under alternate conditions, the mismatched DNA oligonucleotides may still hybridize to the human histamine H3 receptor DNA to permit identification and isolation of human histamine H3 receptor encoding DNA.

DNA encoding human histamine H3 receptor from a particular organism may be used to isolate and purify homologues of human histamine H3 receptor from other organisms. To accomplish this, the first human histamine H3 receptor DNA may be mixed with a sample containing DNA encoding homologues of human histamine H3 receptor under appropriate hybridization conditions. The hybridized DNA complex may be isolated and the DNA encoding the homologous DNA may be purified therefrom.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate or a receptor for a ligand.

As used herein, a "functional derivative" of human histamine H3 receptor is a compound that possesses a biological activity (either functional or structural) that is substantially similar to the biological activity of human histamine H3 receptor. The term "functional derivatives" is intended to include the "fragments," "variants," "degenerate variants," "analogs" and "homologues" or to "chemical derivatives" of human histamine H3 receptor. The term "fragment" is meant to refer to any polypeptide subset of human histamine H3 receptor. The term "variant" is meant to refer to a molecule substantially similar in structure and function to either the entire human histamine H3 receptor molecule or to a fragment thereof. A molecule is "substantially similar" to human histamine H3 receptor if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire human histamine H3 receptor molecule or to a fragment thereof.

Monospecific antibodies to human histamine H3 receptor are purified from mammalian antisera containing antibodies reactive against human histamine H3 receptor or are prepared as monoclonal antibodies reactive with human histamine H3 receptor using the technique of Kohler and Milstein, Nature 256: 495–497 (1975). Monospecific antibody as used herein is defined as a single antibody species or multiple antibody species with homogenous binding characteristics for human histamine H3 receptor. Homogenous binding as used herein refers to the ability of the antibody species to bind to a specific antigen or epitope, such as those associated with the human histamine H3 receptor, as described above. Human histamine H3 receptor specific antibodies are raised by immunizing animals such as mice, rats, guinea pigs, rabbits, goats, horses and the like, with rabbits being preferred, with an appropriate concentration of human histamine H3 receptor either with or without an immune adjuvant.

Preimmune serum is collected prior to the first immunization. Each animal receives between about 0.1 mg and about 1000 mg of human histamine H3 receptor associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of human histamine H3 receptor in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunizaiton. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with human histamine H3 receptor are prepared by immunizing inbred mice, preferably Balb/c, with human histamine H3 receptor and any fragments thereof. The mice are immunized by the IP or SC route with about 0.1 mg to about 10 mg, preferably about 1 mg, of human histamine H3 receptor in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 mg of human histamine H3 receptor in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas.

Fusion partners may include, but are not limited to: mouse myelomas P3/NS1/Ag 4-1; MPC-11; S-194 and Sp 2/0, with Sp 2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using human histamine H3 receptor as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973. Monoclonal antibodies are produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-human histamine H3 receptor mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of human histamine H3 receptor in body fluids or tissue and cell extracts.

It is readily apparent to those skilled in the art that the above described methods for producing monospecific antibodies may be utilized to produce antibodies specific for human histamine H3 receptor polypeptide fragments, or full-length nascent human histamine H3 receptor polypeptide, or the individual human histamine H3 receptor subunits. Specifically, it is readily apparent to those skilled in the art that monospecific antibodies may be generated which are specific for only one human histamine H3 receptor subunit or the fully functional histamine H3 receptor.

DNA clones, termed pH3R, are identified which encode proteins that, when expressed in any recombinant host, including but not limited to mammalian cells or insect cells or bacteria, form a human histamine H3 receptor sensitive to histamine or other histamine H3 ligands, including but not limited to histamine or R-alpha-methylhistamine. The expression of human histamine H3 receptor DNA results in the expression of the properties observed with human histamine H3 receptor. These include: direct activation with histamine or R-alpha-methylhistamine or any other histamine H3 ligand known to those in the field.

Histamine is a biogenic amine transmitter that functions in some capacity in nearly all physiological and pathophysiological situations. Histamine acts as a neurotransmitter and neuromodulator in the central nervous system, mediates inflammatory and allergic responses, regulates airway function, controls acid secretion in the stomach, regulates cardiovascular function as well as arterial and venous responses and is without doubt involved in processes yet to be determined. The histamine receptors that mediate these effects are not completely characterized. One way to understand which histamine receptors are involved in these processes is to develop chemical modulators (agonists, antagonists) of the receptors as research tools and therapeutic entities. Recombinant host cells expressing the human histamine H3 receptor can be used to provide materials for a screeing method to identify such agonists and antagonists. As such, this invention of the human histamine H3 receptor directly teaches a way to identify new agonists and antagonists that may prove useful as research tools or may be used as therapeutics to treat disorders directly or indirectly involving histamine receptors.

The present invention is also directed to methods for screening for compounds which modulate the expression of DNA or RNA encoding human histamine H3 receptor as well as the function of human histamine H3 receptor protein in vivo. Compounds which modulate these activities may be DNA, RNA, peptides, proteins, or non-proteinaceous organic molecules. Compounds may modulate by increasing or attenuating the expression of DNA or RNA encoding human histamine H3 receptor, or the function of human histamine H3 receptor protein. Compounds that modulate the expression of DNA or RNA encoding human histamine H3 receptor or the function of human histamine H3 receptor protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, research tools, and diagnostic agents.

Kits containing human histamine H3 receptor DNA or RNA, antibodies to human histamine H3 receptor, or human histamine H3 receptor protein may be prepared. Such kits are used to detect DNA which hybridizes to human histamine H3 receptor DNA or to detect the presence of human histamine H3 receptor protein or peptide fragments in a sample. Such characterization is useful for a variety of purposes including but not limited to forensic analyses, diagnostic applications, and epidemiological studies.

The DNA molecules, RNA molecules, recombinant protein and antibodies of the present invention may be used to screen and measure levels of human histamine H3 receptor DNA, human histamine H3 receptor RNA or human histamine H3 receptor protein. The recombinant proteins, DNA molecules, RNA molecules and antibodies lend themselves to the formulation of kits suitable for the detection and typing of human histamine H3 receptor. Such a kit would comprise a compartmentalized carrier suitable to hold in close confinement at least one container. The carrier would further comprise reagents such as recombinant human histamine H3 receptor protein or anti-human histamine H3 receptor antibodies suitable for detecting human histamine H3 receptor. The carrier may also contain a means for detection such as labeled antigen or enzyme substrates or the like. Nucleotide sequences that are complementary to the human histamine H3 receptor encoding DNA sequence can be synthesized for antisense therapy.

These antisense molecules may be DNA, stable derivatives of DNA such as phosphorothioates or methylphosphonates, RNA, stable derivatives of RNA such as 2'-O-alkylRNA, or other human histamine H3 receptor antisense oligonucleotide mimetics. Human histamine H3 receptor antisense molecules may be introduced into cells by microinjection, liposome encapsulation or by expression from vectors harboring the antisense sequence. human histamine H3 receptor antisense therapy may be particularly useful for the treatment of diseases where it is beneficial to reduce human histamine H3 receptor activity.

Human histamine H3 receptor gene therapy may be used to introduce human histamine H3 receptor into the cells of target organisms. The human histamine H3 receptor gene can be ligated into viral vectors which mediate transfer of the human histamine H3 receptor DNA by infection of recipient host cells. Suitable viral vectors include retrovirus, adenovirus, adeno-associated virus, herpes virus, vaccinia virus, polio virus and the like. Alternatively, human histamine H3 receptor DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo human histamine H3 receptor gene therapy. Human histamine H3 receptor gene therapy may be particularly useful for the treatment of diseases where it is beneficial to elevate human histamine H3 receptor activity.

Pharmaceutically useful compositions comprising human histamine H3 receptor DNA, human histamine H3 receptor RNA, or human histamine H3 receptor protein, or modulators of human histamine H3 receptor receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of human histamine H3 receptor-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the human histamine H3 receptor receptor or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of human histamine H3 receptor receptors can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a human histamine H3 receptor modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the human histamine H3 receptor receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that is the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The following examples illustrate the present invention without, however, limiting the same thereto.

EXAMPLE 1

Cloning of human histamine H3 receptor DNA (pH3R)

cDNA synthesis:

First strand synthesis: Approximately 5 µg of human thalamus mRNA (Clonetech) was used to synthesize cDNA using the cDNA synthesis kit (Life Technologies). 2 µl of Not1 primer adapter was added to 511 of mRNA and the mixture was heated to 70° C. for 10 minutes and placed on ice. The following reagents were added on ice: 4 µl of 5× first strand buffer (250 mM TRIS-HCl (pH8.3), 375 mM KCl, 15 mMMgCl$_2$), 21 µl of 0.1M DTT, 10 mM dNTP (nucleotide triphosphates) mix and 1 µl of DEPC treated water. The reaction was incubated at 42° C. for 5 minutes. Finally, 5 µl of Superscript RT II was added and incubated at 42° C. for 2 more hours. The reaction was terminated on ice.

Second strand synthesis: The first strand product was adjusted to 931 µl with water and the following reagents were added on ice:30 µl of 5×2nd strand buffer (100 mM TRIS-HCl (pH6.9), 450 mM KCl, 23 mM MgCl$_2$, 0.75 mM β-NAD+, 50 mM (NH4)$_2$SO$_4$), 3 µl of 10 mM dNTP (nucleotide triphosphates), 1 µl *E. coli* DNA ligase (10 units)1 µl RNase H (2units), 4 µl DNA pol I (10 units). The reaction was incubated at 16° C. for 2 hours. The DNA from second strand synthesis was treated with T4 DNA polymerase and placed at 16° C. to blunt the DNA ends. The double stranded cDNA was extracted with 150 μl of a mixture of phenol and chloroform (1:1, v:v) and precipitated with 0.5 volumes of 7.5 M NH4OAc and 2 volumes of absolute ethanol. The pellet was washed with 70% ethanol and dried down at 37° C. to remove the residual ethanol. The double stranded DNA pellet was resuspended in 25 μl of water and the following reagents were added; 10 μl of 5×T4 DNA ligase buffer, 10 μl of Sal1 adapters and 5 μl of T4 DNA ligase. The ingredients were mixed gently and ligated overnight at 16° C. The ligation mix was extracted with phenol:chloroform:isoamyl alcohol, vortexed thoroughly and centrifuged at room temperature for 5 minutes at 14,000× g to separate the phases. The aqueous phase was transferred to a new tube and the volume adjusted to 100 ml with water. The purified DNA was size selected on a chromaspin 1000 column (Clontech) to eliminate the smaller cDNA molecules. The double stranded DNA was digested with Notl restriction enzyme for 3–4 hours at 37° C. The restriction digest was electrophoresed on a 0.8% low melt agarose gel. The cDNA in the range of 1–5 kb was cut out and purified using Gelzyme (Invitrogen). The product was extracted with phenol:chloroform and precipitated with $NH_4OAc$ and absolute ethanol. The pellet was washed with 70% ethanol and resuspended in 10 ml of water.

Ligation of cDNA to the Vector: The cDNA was split up into 5 tubes (2 μl each) and the ligation reactions were set up by adding 4.5 μl of water, 2 μl of 5× ligation buffer, 1 μl of p-Sport vector DNA (cut with Sal-1/Not1 and phosphatase treated) and 0.5 μl of T4 DNA ligase. The ligation was incubated at 40° C. overnight.

Introduction of Ligated cDNA into E. coli by Electroporation:

The ligation reaction volume was adjusted to a total volume of 20 ill with water. Five ml of yeast tRNA, 12.5 ml of 7.5 M $NH_4OAc$ and 70 ml of absolute ethanol (−20° C.) was added. The mixture was vortexed thoroughly, and immediately centrifuged at room temperature for 20 minutes at 14,000× g. The pellets were washed in 70% ethanol and each pellet was resuspended in 5 ml of water. All 5 ligations (25 ml) were pooled and 100 μl of DH10B electrocompetent cells (Life Technologies) were electroporated with 1 ml of DNA (total of 20 electroporations), then plated out on ampicillin plates to determine the number of recombinants (cfu) per μl. The entire library was seeded into 2 liters of Super Broth and maxipreps were made using Promega Maxi Prep kit and purified on cesium chloride gradients.

Screening of library:

1 μl aliquots of the library contructed above were electroporated into Electromax DH10B cells (Life Technologies). The volume was adjusted to 1 ml with SOC media and incubated for 1 hour at 37° C. with shaking. The library was then plated out on 50 150 $cm^2$ plates containing LB to a density of 5000 colonies per plate. These were grown overnight at 37° C.

A histamine H3 receptor probe was generated by polymerase chain reaction using the following primer pair. 5' oligo: 5' ACTGGTACGAAACCTCCTTCTGGCTC 3' [SEQ.ID. NO.: 2] and 3' oligo: 5' CACCCAGCCTC-CAGTCCAGCCAGTGAG 3' [SEQ.ID.NO.: 1]. The final probe sequence is shown in FIG. 6. Amplification was cycled 35 times with a 50–60° C. annealing temperature and human thalamus cDNA as template. The PCR fragment that was generated (400–500 bp) was 32P-labelled using the klenow fragment of DNA polymerase I and a oligo labeling kit (Pharmacia). The fragment was then cleaned by one passage through a S-200 column (Pharmacia).

The library colonies are lifted on nitrocellulose filters and crosslinked via UV irradiation (Stratagene). Filters were washed three times in buffer (50 mM TRIS, 1 M NaCl, 2 mM EDTA, 1% SDS) at 42° C. Filters were then prehybridized in 1:1 Southern Prehyb:Formamide with salmon sperm DNA (50 mg, boiled) for 6 hours at 42° C. Filters were then hybridized with the probe ($1 \times 10^6$ counts/ml) overnight. The filters were then washed one time with 2× SSC/0.2% SDS at room temperature for 15 minutes, 2 times with 0.2× SSC/0.1% SDS at 45° C. for 30 minutes each. Filters were then wrapped in plastic wrap and exposed to film (Kodak) overnight at −80° C.

Positive clones were identified. Resulting positives were cored from the original plate, incubated in LB for 45 minutes at 37° C. and re-plated overnight. The filter lifting/hybridizing/washing/colony picking procedure was replicated until a single clone or clones were isolated, representing an individual cDNA.

From the screen for human histamine H3 receptor, all cDNA clones were isolated and sequenced. One clone, pH3R, contained a 2699 bp insert (FIG. 1). This sequence had an apparent open reading frame from nucleotide 299 to 1335 (FIG. 2). This open reading frame encoded a protein of 445 amino acids (FIG. 3).

EXAMPLE 4

Cloning of human histamine H3 receptor cDNA into a Mammalian Expression Vector

The human histamine H3 receptor cDNAs (collectively referred to as pH3R) were cloned into the mammalian expression vector pCIneo. The human histamine H3 receptor cDNA clone was isolated from the human thalamus cDNA library. The full length cDNA was used as the template for PCR using specific primers with EcoR1 (5'AAC GTT GAA TTC GCC ACC ATG GAG CGC GCG CCG CCC GAC GGG CCG CTG AAC3') [SEQ.ID.NO.:3] and Notl (5'AAC GTT GCG GCC GCA GGC TCT GGT GGG CCA CTC ACT TCC AG3') [SEQ.ID.NO.:4] sites for cloning. The PCR product was purified on a column (Wizard PCR DNA purification kit from Promega) and digested with Not I and EcoR1 (NEB) to create cohesive ends. The product was purified by a low melting agarose gel electrophoresis. The pCIneo vector was digested with EcoR1 and Notl enzymes and subsequently purified on a low melt agarose gel. The linear vector was used to ligate to the human histamine H3 receptor cDNA inserts. Recombinants were isolated, designated human histamine H3 receptor, and used to transfect mammalian cells (L-cells) by $CaPO_4$-DNA precipitation. Stable cell clones were selected by growth in the presence of G418. Single G418 resistant clones were isolated and shown to contain the intact human histamine H3 receptor gene. Clones containing the human histamine H3 receptor cDNAs were analyzed for pH3R expression by measuring inhibition of adenylate cyclase in response to histamine (FIG. 5) according to the method of (Konig, Mahan et al. 1991) or by directly measuring cAMP accumulation by radioimmunoassay using Flashplates (NEN). Expression was also analyzed using [$^3$H]-N-alpha-methylhistamine binding assays (Clark, Korte et al. 1992). Recombinant plasmids containing human histamine H3 receptor encoding DNA were used to transform the mammalian COS or CHO cells or HEK293 or L-cells.

Cells expressing human histamine H3 receptor, stably or transiently, are used to test for expression of human histamine H3 receptor and for [$^3$H]-N-alpha-methylhistamine binding activity. These cells are used to identify and examine other compounds for their ability to modulate, inhibit or activate the human histamine H3 receptor and to compete for radioactive histamine binding.

Cassettes containing the human histamine H3 receptor cDNA in the positive orientation with respect to the promoter are ligated into appropriate restriction sites 3' of the promoter and identified by restriction site mapping and/or sequencing. These cDNA expression vectors are introduced into fibroblastic host cells for example COS-7 (ATCC# CRL1651), and CV-1 tat [Sackevitz et al., Science 238: 1575 (1987)], 293, L (ATCC# CRL6362)] by standard methods including but not limited to electroporation, or chemical procedures (cationic liposomes, DEAE dextran, calcium phosphate). Transfected cells and cell culture supernatants are harvested and analyzed for human histamine H3 receptor expression as described herein.

All of the vectors used for mammalian transient expression can be used to establish stable cell lines expressing human histamine H3 receptor. Unaltered human histamine H3 receptor cDNA constructs cloned into expression vectors are expected to program host cells to make human histamine H3 receptor protein.

The transfection host cells include, but are not limited to, CV-1-P [Sackevitz et al., Science 238: 1575 (1987)], tk-L [Wigler, et al. Cell 11: 223 (1977)], NS/0, and dHFr-CHO [Kaufmnan and Sharp, J. Mol. Biol. 159: 601, (1982)].

Co-transfection of any vector containing human histamine H3 receptor cDNA with a drug selection plasmid including, but not limited to G418, aminoglycoside phosphotransferase; hygromycin, hygromycin-B phospholransferase; APRT, xanthine-guanine phosphoribosyl-transferase, will allow for the selection of stably transfected clones. Levels of human histamine H3 receptor are quantitated by the assays described herein.

Human histamine H3 receptor cDNA constructs are also ligated into vectors containing amplifiable drug-resistance markers for the production of mammalian cell clones synthesizing the highest possible levels of human histamine H3 receptor. Following introduction of these constructs into cells, clones containing the plasmid are selected with the appropriate agent, and isolation of an over-expressing clone with a high copy number of plasmids is accomplished by selection in increasing doses of the agent.

The expression of recombinant human histamine H3 receptor is achieved by transfection of full-length human histamine H3 receptor cDNA into a mammalian host cell.
Characterization Of human histamine H3 receptor Mouse L cells were transfected with pH3R and selected in the presence of neomycin for 10 days. Individual colonies were picked and grown in 6well dishes. Cells were then plated onto 96-well plates and grown to confluency. Cells were incubated for 20 minutes with isobutylmethylxanthine (1 mM). Cells were then stimulated with histamine (100 nM–100 uM) for 5 minutes. Cells were then stimulated with forskolin (3 uM) and allowed to incubate at 37° C. for 20 minutes. Cells were then treated with 0.1N hydrochloric acid. Cells were then frozen and thawed. Aliquots of the supernatant were then analyzed for their cyclic AMP content using a standard cAMP radioimmunoassay kit (Flashplates, NEN). The forskolin treatment raises the intracellular concentration of cAMP. Any cells that responded to histamine by decreasing the cAMP content in response to forskolin were considered to be expressing active functional human histamine H3 receptor.

The recombinant human histamine H3 receptor expressed from the human histamine H3 receptor-encoding DNA molecule described herein was shown to be specifically activated by a histamine H3 receptor agonist and was also shown to be inhibited by a histamine H3 receptor antagonist.

EXAMPLE 5

Figure 7A:
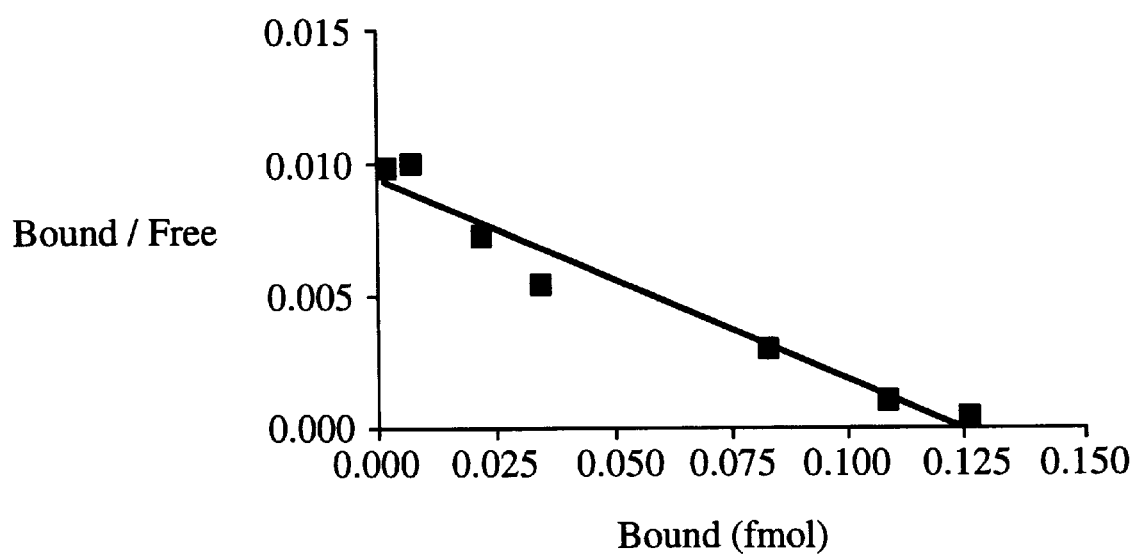
FIG. 7 Panel A and Panel B—Saturation binding of [$^3$H]-N-alpha-methyl-histamine to pH3R expressing L cells is shown.
Figure 7B:
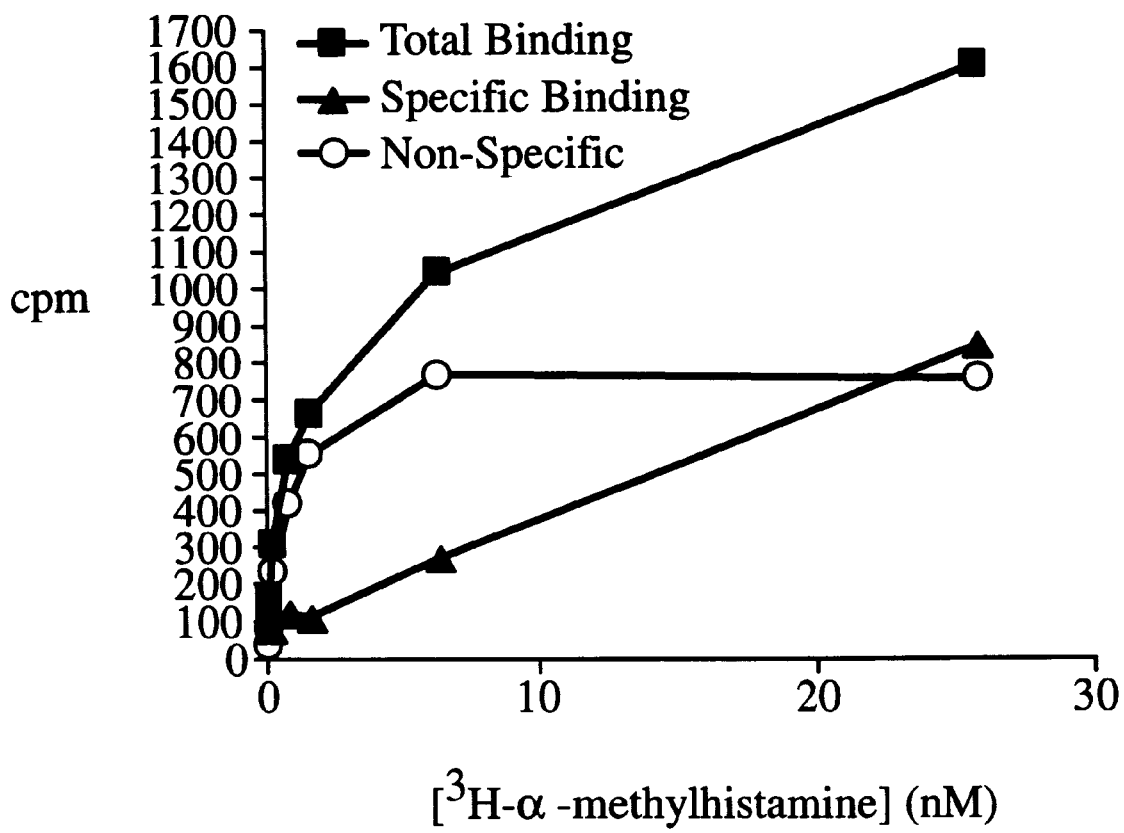

Binding assay on recombinant human histamine H3 receptor L cells that inhibited forskolin-stimulated cAMP accumulation as described above were grown in 150 cm2 tissue culture dishes. Cells were washed with saline solution, scraped with a cell scraper and collected by centrifugation (1000 rpm, 5 min). L cells expressing human histamine H3 receptor bound $^3$H-N-alpha-methylhistamine with high affinity (FIG. 7). Cell membranes were prepared by homogenization of the cell pellet in 20 mM TRIS-HCl with a polytron tissue homogenizer for 10 seconds at high speed. Homogenate was centrifuged at 1000 rpm for 5 minutes at 4° C. The supernatant was then collected and centrifuged at 20,000× g for 25 minutes at 4° C. The final pellet is resuspended in 50 mM Tris-HCl. Cell membranes were incubated with $^3$H-N-alpha-methylhistamine (0.01 nM–25 nM) in the presence or absence of excess histamine (10000 nM). Incubation was done at room temperature for 45 minutes. Membranes were harvested by rapid filtration over Whatman GF/C filters and washed 4 times with ice cold 50 mM TRIS HCl. Filters were then dried, mixed with scintillant and counted for radioactivity. L cells expressing human histamine H3 receptor were used to measure the affinity of binding of other compounds and their ability to displace $^3$H-ligand binding by incubating the above described reaction in the presence of various concentrations of inhibitor or compound to be tested.

EXAMPLE 6

Primary Structure Of The human histamine H3 receptor Protein

The nucleotide sequences of pH3R receptor revealed a single large open reading frame of about 1335 base pairs. The cDNA's have 5' and 3'-untranslated extensions of about 298 and about 1066 nucleotides for pH3R. The first in-frame methionine was designated as the initiation codon for an open reading frame that predicts a human histamine H3 receptor protein with an estimated molecular mass (Mr) of about 48656.

The predicted human histamine H3 receptor protein was aligned with nucleotide and protein databases and found to be related to the human histamine H1 and human histamine H2 receptors. Approximately 25% of the amino acids in human histamine H3 receptor were highly conserved, showing at least 25% amino acid identity within the histamine H2 receptor, 28% with the histamine H1 receptor, and approximately 25% with the family of biogenic amine G-protein coupled receptors. The conserved motifs found in this family of receptors, such as seven conserved hydrophobic domains , were also found in the human histamine H3 receptor sequence. The human histamine H3 receptor protein contained the conserved aspartate residue found in the $3^{rd}$ transmembrane domain of all biogenic amine receptors. The human histamine H3 receptor protein contained the conserved asparagine residue found in the $1^{st}$ transmembrane domain of all biogenic amine receptors. The human histamine H3 receptor protein contained the conserved arginine residue found in the $3^{rd}$ transmembrane domain of all biogenic amine receptors. The human histamine H3 receptor protein contained the conserved tryptophan residue found in the $4^{th}$ transmembrane domain of all biogenic amine receptors. The human histamine H3 receptor protein contained the conserved phenylalanine residue found in the $5^{th}$ transmembrane domain of all biogenic amine receptors. The human histamine H3 receptor protein contained the conserved proline residue found in the $6^{th}$ transmembrane domain of all biogenic amine receptors. The human histamine H3 receptor protein contained the conserved tyrosine residue found in the $7^{th}$ transmembrane domain of all biogenic amine receptors.

EXAMPLE 7

Cloning of the human histamine H3 receptor cDNA into *E. coli* Expression Vectors Recombinant human histamine H3 receptor is produced in E. coli following the transfer of the human histamine H3 receptor expression cassette into E. coli expression vectors, including but not limited to, the pET series (Novagen). The pET vectors place human histamine H3 receptor expression under control of the tightly regulated bacteriophage T7 promoter. Following transfer of this construct into an E. coli host which contains a chromosomal copy of the T7 RNA polymerase gene driven by the inducible lac promoter, expression of human histamine H3 receptor is induced when an appropriate lac substrate (IPTG) is added to the culture. The levels of expressed human histamine H3 receptor are determined by the assays described herein.

The cDNA encoding the entire open reading frame for human histamine H3 receptor is inserted into the NdeI site of pET [16]11a. Constructs in the positive orientation are identified by sequence analysis and used to transform the expression host strain BL21. Transformants are then used to inoculate cultures for the production of human histamine H3 receptor protein. Cultures may be grown in M9 or ZB media, whose formulation is known to those skilled in the art. After growth to an $OD_{600}=1.5$, expression of human histamine H3 receptor is induced with 1 mM IPTG for 3 hours at 37° C.

EXAMPLE 8
Cloning of human histamine H3 receptor cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing human histamine H3 receptor cDNA is produced by the following standard methods (InVitrogen Maxbac Manual): the human histamine H3 receptor cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P.A., Nuc. Acid. Res. 18: 5667 (1990)] into Sf9 cells. Recombinant pAC360 viruses are identified by the absence of inclusion bodies in infected cells and recombinant pBlue-Bac viruses are identified on the basis of β-galactosidase expression (Summers, M. D. and Smith, G. E., Texas Agriculture Exp. Station Bulletin No. 1555). Following plaque purification, human histamine H3 receptor expression is measured by the assays described herein.

The cDNA encoding the entire open reading frame for human histamine H3 receptor is inserted into the BamHI site of pBlueBacII. Constructs in the positive orientation are identified by sequence analysis and used to transfect Sf9 cells in the presence of linear AcNPV mild type DNA.

Authentic, active human histamine H3 receptor is found in the cytoplasm of infected cells. Active human histamine H3 receptor is extracted from infected cells by hypotonic or detergent lysis.

EXAMPLE 9
Cloning of human histamine H3 receptor cDNA into a yeast expression vector Recombinant human histamine H3 receptor is produced in the yeast S. cerevisiae following the insertion of the optimal human histamine H3 receptor cDNA cistron into expression vectors designed to direct the intracellular or extracellular expression of heterologous proteins. In the case of intracellular expression, vectors such as EmBLyex4 or the like are ligated to the human histamine H3 receptor cistron [Rinas, U. et al., Biotechnology 8: 543–545 (1990); Horowitz B. et al., J. Biol. Chem. 265: 4189-4192 (1989)]. For extracellular expression, the human histamine H3 receptor cistron is ligated into yeast expression vectors which fuse a secretion signal (a yeast or mammalian peptide) to the $NH_2$ terminus of the human histamine H3 receptor protein [Jacobson, M. A., Gene 85: 511–516 (1989); Riett L. and Bellon N. Biochem. 28: 2941–2949 (1989)].

These vectors include, but are not limited to pAVE1>6, which fuses the human serum albumin signal to the expressed cDNA [Steep O. Biotechnology 8: 42–46 (1990)], and the vector pL8PL which fuses the human lysozyme signal to the expressed cDNA [Yamamoto, Y., Biochem. 28: 2728–2732)]. In addition, human histamine H3 receptor is expressed in yeast as a fusion protein conjugated to ubiquitin utilizing the vector pVEP [Ecker, D. J., J. Biol. Chem. 264: 7715–7719 (1989), Sabin, E. A., Biotechnology 7: 705–709 (1989), McDonnell D. P., Mol. Cell Biol. 9: 5517–5523 (1989)]. The levels of expressed human histamine H3 receptor are determined by the assays described herein.

REFERENCES

Arrang, J. M., M. Garbarg, et al. (1983). "Autoinhibition of brain histamine release mediated by a novel class (H3) of histamine receptor." *Nature* (London) 302(5911): 832–7.

Clark, M. A., A. Korte, et al. (1993). "Guanine nucleotides and pertussis toxin reduce the affinity of histamine H3 receptors on AtT-20 cells." *Agents Actions* 40(3–4): 129–34.

Clark, M. A., A. Korte, et al. (1992). "High affinity histamine H3 receptors regulate ACTH release by AtT-20 cells." *Eur. J. Pharmacol.* 210(1): 31–5.

Gantz, I., M. Schaffer, et al. (1991). "Molecular cloning of a gene encoding the histamine H2 receptor." *Proc. Natl. Acad. Sci. U.S.A.* 88(2): 429–33.

Hill, S. J., C. R. Ganellin, et al. (1997). "International Union of Pharmacology. XIII. Classification of histamine receptors." *Pharmacol. Rev.* 49(3): 253–278.

Konig, M., L. C. Mahan, et al. (1991). "Method for identifying ligands that bind to cloned Gs- or Gi-coupled receptors." *Mol. Cell. Neurosci.* 2(4): 331–7.

Pollard, H., J. Moreau, et al. (1993). "A detailed autoradiographic mapping of histamine H3 receptors in rat brain areas." *Neuroscience* (Oxford) 52(1): 169–89.

Yamashita, M., H. Fukui, et al. (1991). "Expression cloning of a cDNA encoding the bovine histamine H1 receptor." *Proc. Natl. Acad. Sci. U.S.A.* 88(24): 11515–19.

What is claimed is:

1. An isolated and purified cDNA molecule having a nucleotide sequence selected from a group consisting of: (SEQ.ID.NO.:5); and (SEQ.ID.NO.:6).

2. An expression vector comprising a nucleotide sequence selected from a group consisting of: (SEQ.ID.NO.:5); and (SEQ.ID.NO.:6).

3. A recombinant host cell comprising a nucleotide sequence selected from a group consisting of: (SEQ.ID.NO.:5); and (SEQ.ID.NO.:6).

4. A process for expression of human histamine H3 receptor protein comprising:

(a) transferring the expression vector of claim 2 into suitable host cells; and (b) culturing the host cells of step (a) under conditions which allow expression of the human histamine H3 receptor protein from the expression vector.

* * * * *